US009844455B2

(12) United States Patent
Bradshaw

(10) Patent No.: US 9,844,455 B2
(45) Date of Patent: *Dec. 19, 2017

(54) ANKLE-FOOT ORTHOSIS

(71) Applicant: Scott Orthotics, LLC, Spearfish, SD (US)

(72) Inventor: Jason L. Bradshaw, Eaton, CO (US)

(73) Assignee: Scott Orthotics, LLC, Spearfish, SD (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/923,315

(22) Filed: Oct. 26, 2015

(65) Prior Publication Data

US 2016/0051390 A1    Feb. 25, 2016

Related U.S. Application Data

(63) Continuation of application No. 14/060,885, filed on Oct. 23, 2013, now Pat. No. 9,168,166, which is a continuation of application No. 29/468,465, filed on Sep. 30, 2013, now Pat. No. Des. 706,942, which is a continuation of application No. 29/448,501, filed on Mar. 12, 2013, now Pat. No. Des. 693,471.

(51) Int. Cl.
| A61F 5/00 | (2006.01) |
|---|---|
| A61F 5/01 | (2006.01) |
| A61F 5/058 | (2006.01) |
| A43B 7/00 | (2006.01) |
| A43B 7/18 | (2006.01) |
| A43B 7/20 | (2006.01) |

(52) U.S. Cl.
CPC .............. *A61F 5/0195* (2013.01); *A61F 5/00* (2013.01); *A61F 5/01* (2013.01); *A61F 5/0102* (2013.01); *A61F 5/0111* (2013.01); *A61F 5/0127* (2013.01); *A61F 5/0585* (2013.01); *A43B 7/00* (2013.01); *A43B 7/18* (2013.01); *A43B 7/20* (2013.01)

(58) Field of Classification Search
CPC .. A61F 5/00; A61F 5/01; A61F 5/0102; A61F 5/0111; A61F 5/0127; A61F 5/0195; A61F 5/0585; A43B 7/00; A43B 7/14; A43B 7/18; A43B 7/20
USPC ..... 602/23, 27, 28; 36/88, 89, 140, 145, 148
See application file for complete search history.

(56) References Cited

U.S. PATENT DOCUMENTS

| 2,320,800 | A | * | 6/1943 | Sabel ................. A43B 7/00 36/140 |
|---|---|---|---|---|
| 3,805,773 | A | * | 4/1974 | Sichau ............... A61F 5/0127 602/28 |
| 4,771,768 | A | | 9/1988 | Crispin |
| 6,976,972 | B2 | | 12/2005 | Bradshaw |
| 6,994,681 | B2 | | 2/2006 | Slautterback et al. |
| D693,471 | S | | 11/2013 | Bradshaw |
| D706,942 | S | | 6/2014 | Bradshaw |
| 9,168,166 | B2 | | 10/2015 | Bradshaw |
| 2006/0116617 | A1 | | 6/2006 | Bradshaw |

* cited by examiner

*Primary Examiner* — Keri J Nelson
(74) *Attorney, Agent, or Firm* — Craig R. Miles; CR Miles P.C.

(57) ABSTRACT

An inventive ankle-foot orthosis which transfers a portion of a wearer's weight normally applied to a wearer's foot and ankle to a wearer's calf thereby removing weight bearing stress from the wearer's foot and ankle.

23 Claims, 12 Drawing Sheets

ANKLE-FOOT ORTHOSIS

This U.S. patent application is a continuation of U.S. patent application Ser. No. 14/060,885, filed Oct. 23, 2013, now U.S. Pat. No. 9,168,166, issued Oct. 24, 2015, which is a continuation of United States Design Patent Application No. 29/468,465, filed Sep. 30, 2013, now U.S. Pat. No. D706,942, issued Jun. 10, 2014, which is a continuation of United States Design Patent Application No. 29/448,501, filed Mar. 12, 2013, now U.S. Pat. No. D693,471, issued Nov. 12, 2013, each hereby incorporated by reference herein.

I. FIELD OF THE INVENTION

An inventive ankle-foot orthosis which transfers a portion of a wearer's weight normally applied to a wearer's foot and ankle to a wearer's calf thereby removing weight bearing stress from the wearer's foot and ankle.

II. BACKGROUND OF THE INVENTION

Many people and diabetics in particular develop sores or ulcers on the soles of their feet. To heal, they must either stay off their feet altogether or use a pressure relieving orthosis. Conventional suspension walkers provide a cuff member configured to lace to the wearer's calf. Upright brace members coupled in fixed unmoving relation to a hard outer boot shell extend upwardly to secure to the cuff member secured to the wearer's calf. A discrete soft boot encloses the wearer's foot which is then nested within the hard, outer boot shell.

III. SUMMARY OF THE INVENTION

A primary object of particular embodiments of the invention can be to provide an ankle-foot orthosis having an upper secured to an insole in a combination having a configuration adapted to receive a wearer's foot and a stirrup including a stirrup base connected between a pair of stirrup side pieces with the stirrup base coupled below the insole to dispose the stirrup in fixed relation to the combination with the pair of stirrup side pieces each upwardly extending to positions adjacent each side of the combination which correspondingly couple to a pair brace members. The wearer's weight supported by the cuff member secured to the pair of braces is correspondingly transferred to the stirrup base disposed below the insole, thereby avoiding any substantial transfer of forces from the stirrup or other components of the assembled ortosis to the combination. This structural relationship avoids the use of a conventional rigid outer boot shell to which conventional braces attach and the use of a discrete soft boot which is received within the rigid outer boot shell to receive the wearer's foot.

Another object of particular embodiments of the invention can be to further comprising a pair of joint elements which correspondingly couple the pair of stirrup side pieces and the pair of brace members allowing rotation of the pair of brace members about an axis extending through the pair of stirrup side pieces allowing corresponding dorsiflexion and plantarflexion of said wear's foot within the combination during use of the ankle-foot orthosis.

Another object of particular embodiments of the invention can be to avoid securing the cuff member to the wearer's calf by the use of laces by configuring the cuff member to dispose a pair of cuff edges disposed in opposed relation a distance apart and by providing a plurality of straps which act on the cuff member to reduce said distance between said pair of cuff edges to secure said cuff member about said wearer's calf.

Another object of particular embodiments of the invention can be to terminate the topline of the combination in opposed relation a distance apart over the dorsum of the wearer's foot leaving the wearer's forefoot uncovered to avoid enclosing the wearer's foot within a closed toe boot.

Naturally, further objects of the invention are disclosed throughout other areas of the specification, drawings, photographs, and claims.

IV. BRIEF DESCRIPTION OF THE DRAWINGS

V. DETAILED DESCRIPTION OF THE INVENTION

Figure 1:
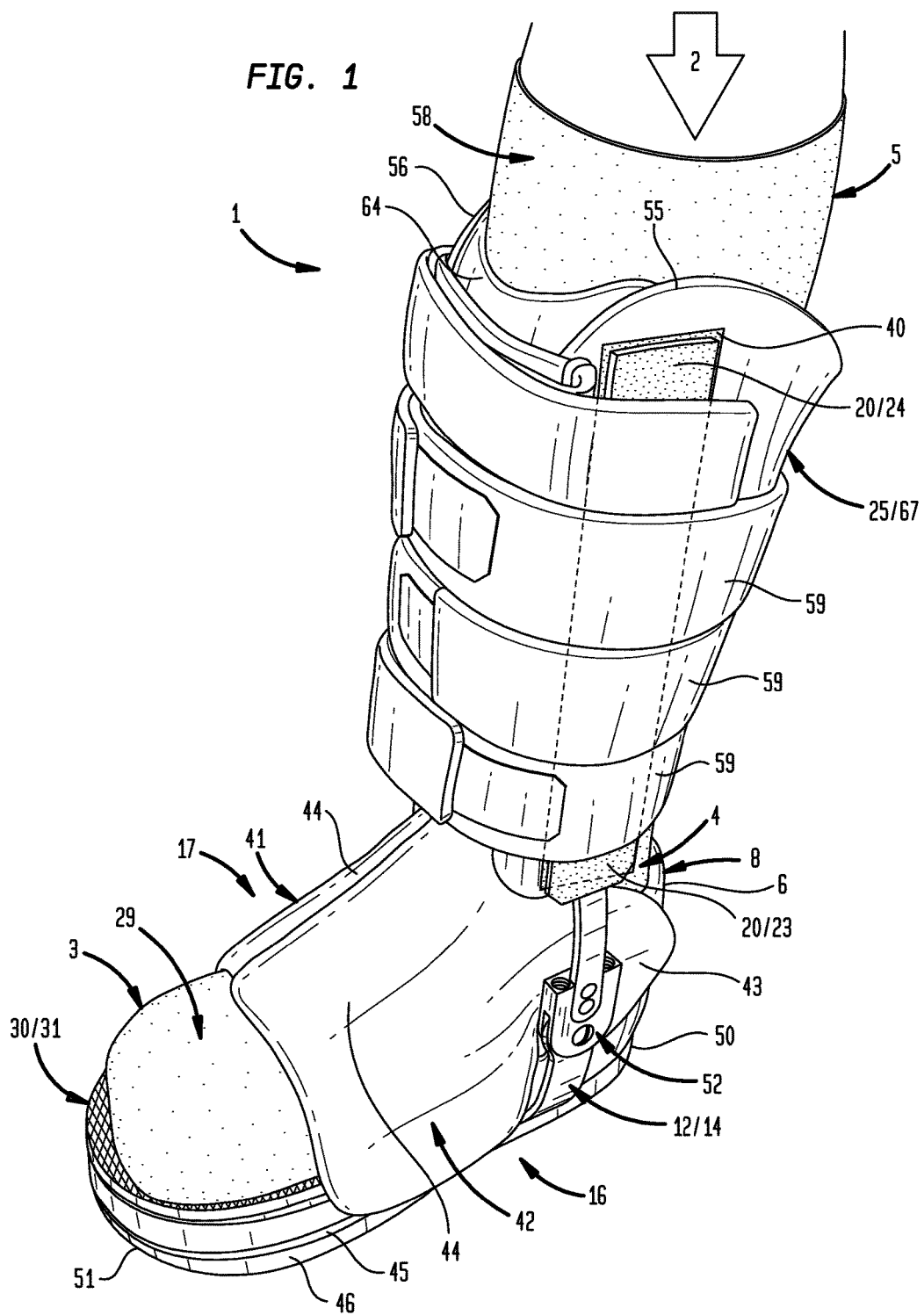
FIG. 1 is a perspective view of a particular embodiment of an inventive ankle-foot orthosis which transfers a portion of a wearer's weight normally applied to a wearer's foot and ankle to a wearer's calf.

Generally referring to FIGS. 1 through 13, an inventive ankle-foot orthosis (1) (also referred to as the "orthosis") is shown having a configuration which transfers a portion of a wearer's weight (2) normally applied to a wearer's foot (3) and ankle (4) to a wearer's calf (5) thereby removing weight bearing stress from the wearer's foot (3) and ankle (4).

Figure 2:
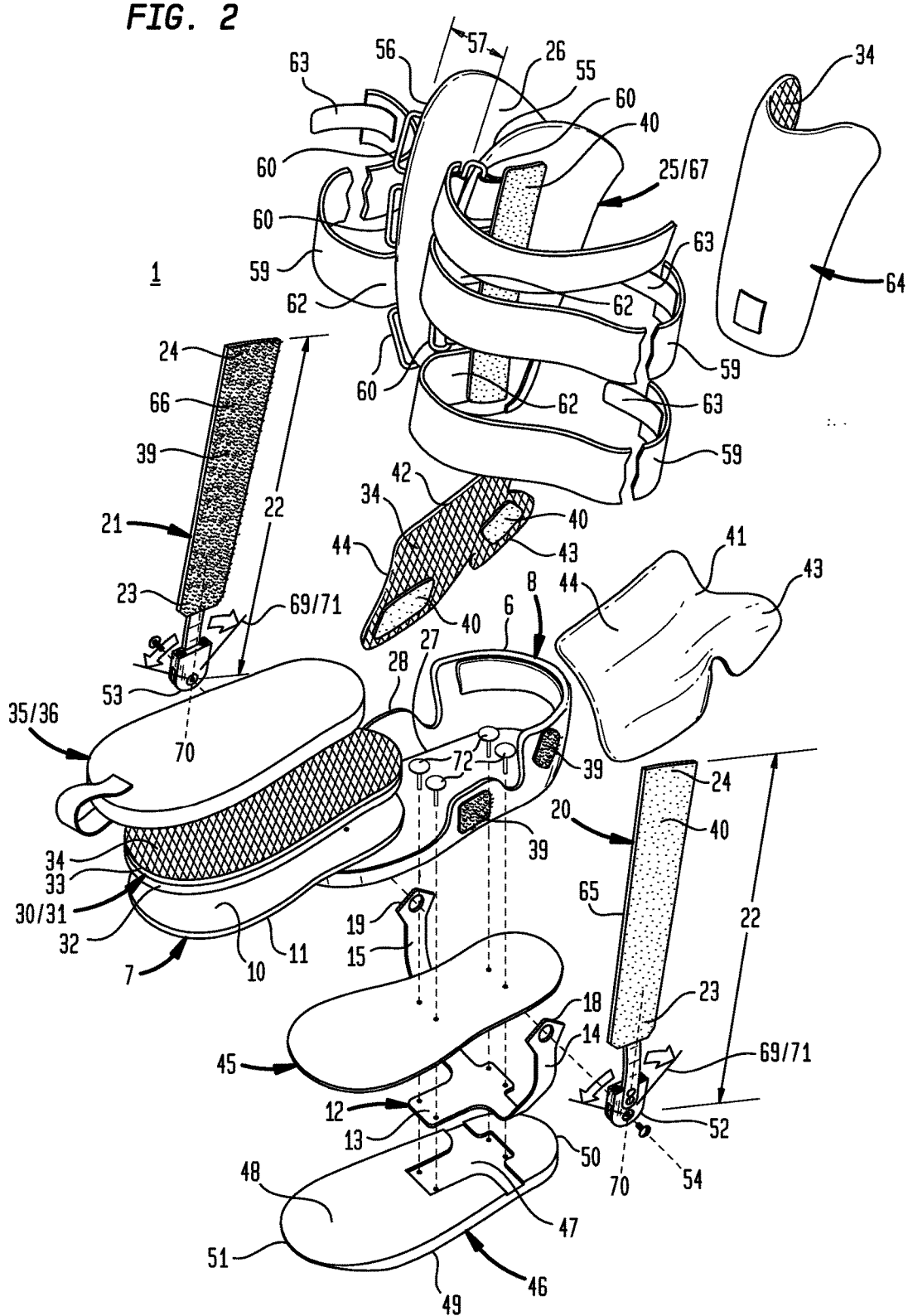
FIG. 2 is an exploded view of the particular embodiment of the ankle-foot orthosis shown in FIG. 1.
Figure 3:
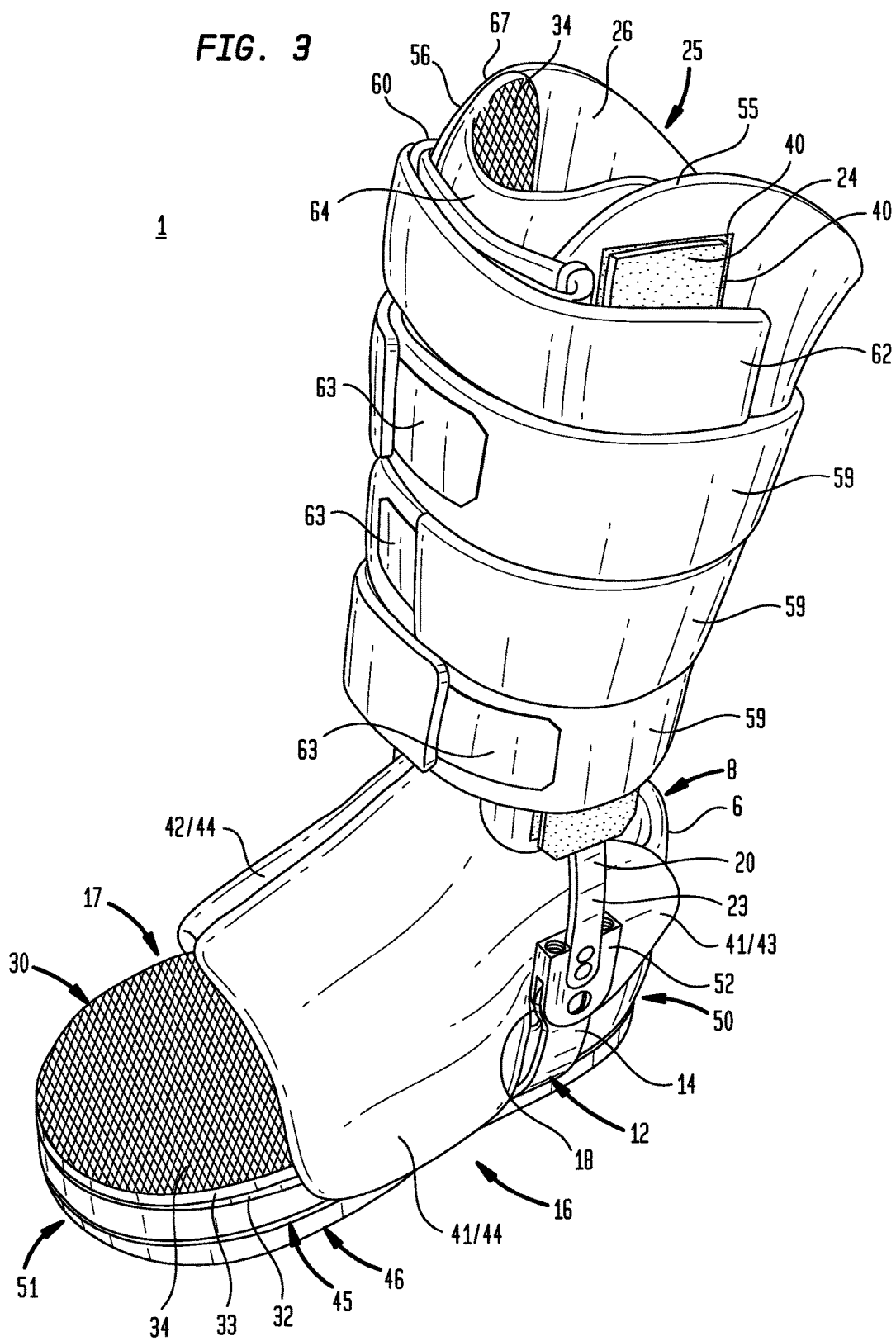
FIG. 3 is a perspective view of a particular embodiment of an inventive ankle-foot orthosis.
Figure 4:
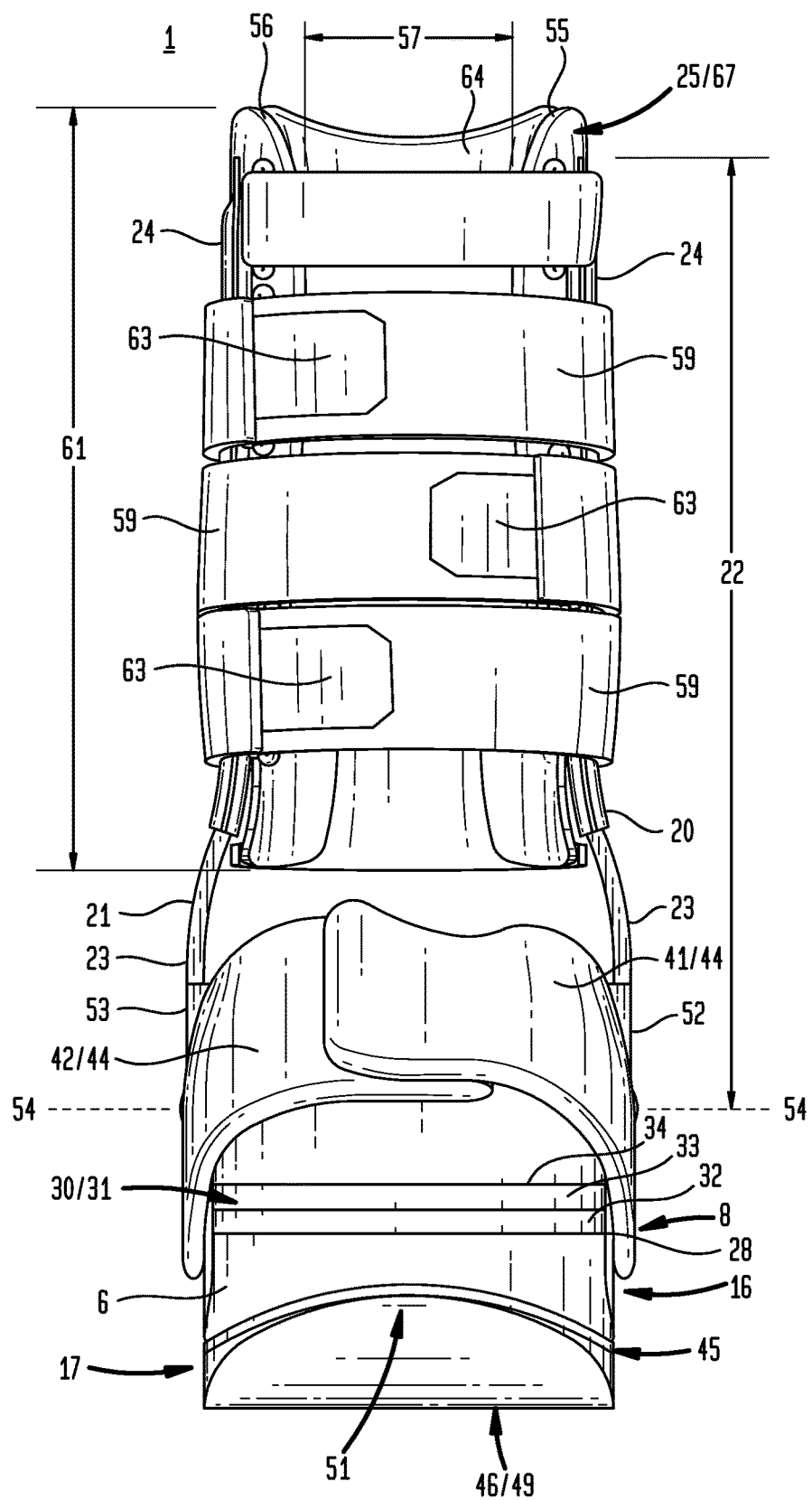
FIG. 4 is a front end view of a particular embodiment of an inventive ankle-foot orthosis.
Figure 5:
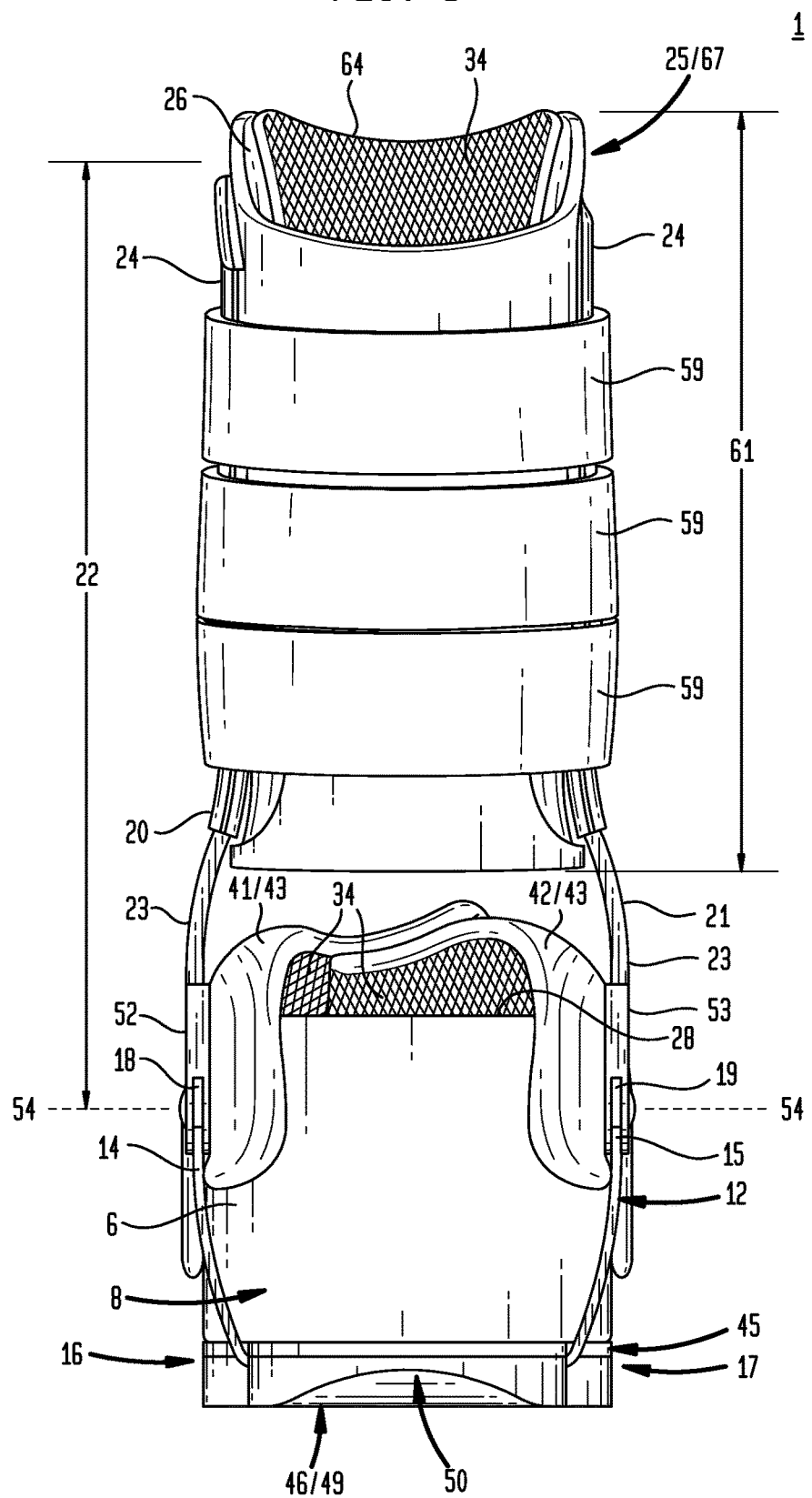
FIG. 5 is a rear end view of a particular embodiment of an inventive ankle-foot orthosis.

Now referring primarily to FIGS. 1 through 9, particular embodiments of the orthosis (1) can include an upper (6) secured to an insole (7) in a combination (8) having a configuration adapted to receive a wearer's foot (3) (as shown in the example of FIG. 1). The insole (7) can have an insole thickness (9) disposed between an insole inner face (10) and an insole outer face (11). A stirrup (12) including a stirrup base (13) connected between a pair of stirrup side pieces (14)(15) can be coupled below the insole outer face (11) to dispose the stirrup (12) in fixed relation to the combination (8) with the pair of stirrup side pieces (14)(15) each upwardly extending to positions adjacent each of the medial side (16) and the lateral side (17) (also referred to as "sides") of the combination (8) (as shown in the example of FIGS. 1 and 2). The pair of stirrup side pieces (14)(15) can correspondingly terminate in a pair of stirrup ends (18)(19) (as shown in the example of FIG. 2). A pair of brace members (20)(21) each having a brace length (22) disposed between a brace member first end (23) and a brace member second end (24) can be correspondingly coupled by brace member first ends (23) to the pair of stirrup ends (18)(19) to dispose the pair of brace members (20)(21) adjacent corresponding sides of the combination (8) with the pair of brace members (20)(21) extending upwardly to positions adjacent each side of the wearer's calf (5) (as shown in the examples of FIGS. 1 and 2). A cuff member (25) can be removably secured to the pair of brace members (20)(21) (as shown in the examples of FIGS. 1 and 2). The cuff member (25) has a cuff internal surface (26) configured to engage the wearer's calf (5). The cuff member (25) engaged to the wearer's calf (5) and secured to the pair of brace members (20)(21) can transfer a portion of the wearer's weight (2) normally applied to the wearer's foot (3) to the wearer's calf (5). The wearer's weight (2) supported by the cuff member (25) secured to the pair of braces (20)(21) and correspondingly transferred to the stirrup (12) disposed below the insole (7) avoids any substantial transfer of forces from the stirrup (12) (or other components of the assembled orthosis (1)) to the combination (8). This structural relationship avoids the use of a conventional rigid outer boot shell to which conventional braces attach and the use of a discrete soft boot which is received within the rigid outer boot shell as described for example by U.S. Pat. No. 6,976,972.

Again referring primarily to FIG. 2, the insole (7) for the purposes of this invention can be made from a substantially flat sheet material such as fiber board, press paper board, plastic, leather, or the like, having an insole periphery (27) which defines the area of the insole upper face (10) and about which the upper (6) secures. The upper (6) can be made from a numerous and wide variety of materials compatible with the method of securing the upper (6) about the insole periphery (27) and retaining the wearer's foot (3) within the combination (8). As shown in the example of FIG. 2, the upper (6) extends upward from the insole (7) and can have a configuration to wrap around the wearer's heel (28) and ankle (4) terminating in an topline (28) disposed in opposed relation a distance apart over the dorsum (29) of the wearer's foot (3) leaving the wearer's forefoot (31) uncovered as shown in the example of FIG. 1.

Again referring primarily to FIG. 2, particular embodiments can further include a main pad (30) which can be disposed over the insole (7) in the upper (6). The main pad (30) can comprise one or more layers (31) of compressible material which can cushion engagement of the wearer's foot (3) with the insole (7). With respect to the main pad (30) shown in the Figures, a first layer of compressible material (32) can overlay the insole (7). A second layer of compressible material (33) having greater firmness can be, but is not necessarily, coupled to the first layer of compressible material (32). The main pad (30) can further include an antimicrobial layer (34) coupled to either of the first layer of compressible material (32) or the second layer of compressible material (33) depending upon the embodiment. As to particular embodiments, an antimicrobial lining (34) can be coupled to a tongue (64) of the orthosis (1) which engages the wearer's tibia or can be coupled to an upper inner surface (73) of an upper (6) which engages the wearer's foot (3). The antimicrobial layer (34) can but is not necessarily a silver metal fiber woven directly into the material to produce a fabric such as X-STATIC® available from Noble Biomaterials, Inc.

Again referring primarily to FIG. 2, particular embodiments can further include one or more fitting pads (35) which removably overlay the main pad (30) to assist in fitting the orthosis (1). The one or more fitting pads (35) can be made as thick or thin as needed to fit the orthosis (1) to transfer a greater or lesser portion of the wearer's weight (2) to the wearer's calf (5). As to particular embodiments, a first fitting pad (36) can be laid over the main pad (30) and a second fitting pad (37) (or any additional number of them) can be placed atop the first fitting pad (36). As one illustrative example, the first fitting pad (36) can be one-half inch thick and the second fitting pad (37) can be one-quarter inch thick. The first and second fitting pads (36)(37) can be used individually to provide discrete one-half inch or discrete one-quarter inch adjustments between the insole inner face (10) and the sole (38) of the wearer's foot (3) or the first fitting pad (36) can overlay the second fitting pads (37) to provide an adjustment of three-quarters inch between the insole inner face (10) and the sole (38) of the wearer's foot (3). Adjustment of the distance between the sole (38) of the wear's foot (3) and the insole inner face (10) correspondingly positions the cuff member (25) for securement to the pair of brace members (20)(21). By use of one or more fitting pads (35), as above described, the cuff member (25) can be adjustably positioned along the brace length (22) of the pair of brace members (20)(21) as precisely as necessary to fit the orthosis (1). As to particular embodiments, the cuff member (25) can be positioned at virtually any desired location vertically along each of the pair of brace members (20)(21) within the overlapping limits of a mateable hook (39) and loop fasteners (40) correspondingly coupled to the cuff member (24) and each of the pair of brace members (20)(21). Also, while mateable hook and loop fasteners (39)(40) are shown in the Figures; this is not intended to limit the invention solely to the use of mateable hook and loop fasteners (39)(40), but rather any other releasable securing fasteners can be used in embodiments of the invention.

Again referring primarily to FIGS. 1 through 9, the orthosis (1) can further include a pair of dorsum flaps (41)(42) each having a flap first portion (43) releasably securable at a position adjacent corresponding sides (16)(17) of the upper (6). The pair of dorsum flaps (41)(42) can each have a flap second portion (44) configured to releasably secure in overlaid relation over the dorsum (29) of the wearer's foot (3) received within the combination (8). As to particular embodiments, the flap first portions (43) of the pair of dorsum flaps (41)(42) adjustably position adjacent corresponding sides (16)(17) of the upper (6) to accommodate greater or lesser size of the wearer's foot (3) and ankle (4). As one example, mateable portions of hook and loop fasteners (39)(40) correspondingly coupled to the sides (16)(17) of the upper (6) and the flap first portions (43) can allow adjustable positioning of the flap first portions (43) with respect to the sides (16)(17) of the upper (6). Similarly, the flap second portions (44) can include mateable portions of hook and loop fasteners (39)(40) which releasably secure the second portions (44) in overlaid relation over the dorsum (29) of said wearer's foot (3) received within the combination (8).

Now referring primarily to FIG. 2, particular embodiments can, but not necessarily include, a midsole (45) secured between the insole (7) and the stirrup base (13). The midsole (45) can be secured to the insole (7) by adhesive, stitching or other suitable securement elements. Mechanical fasteners (72) such as rivets can extend through the insole (7) and the midsole (45) and the stirrup base (13) to couple the stirrup base (13) adjacent the midsole (45) to dispose the stirrup side pieces (14)(15) on the corresponding medial side (16) and lateral side (17) of the combination (8), as above described.

Figure 6:
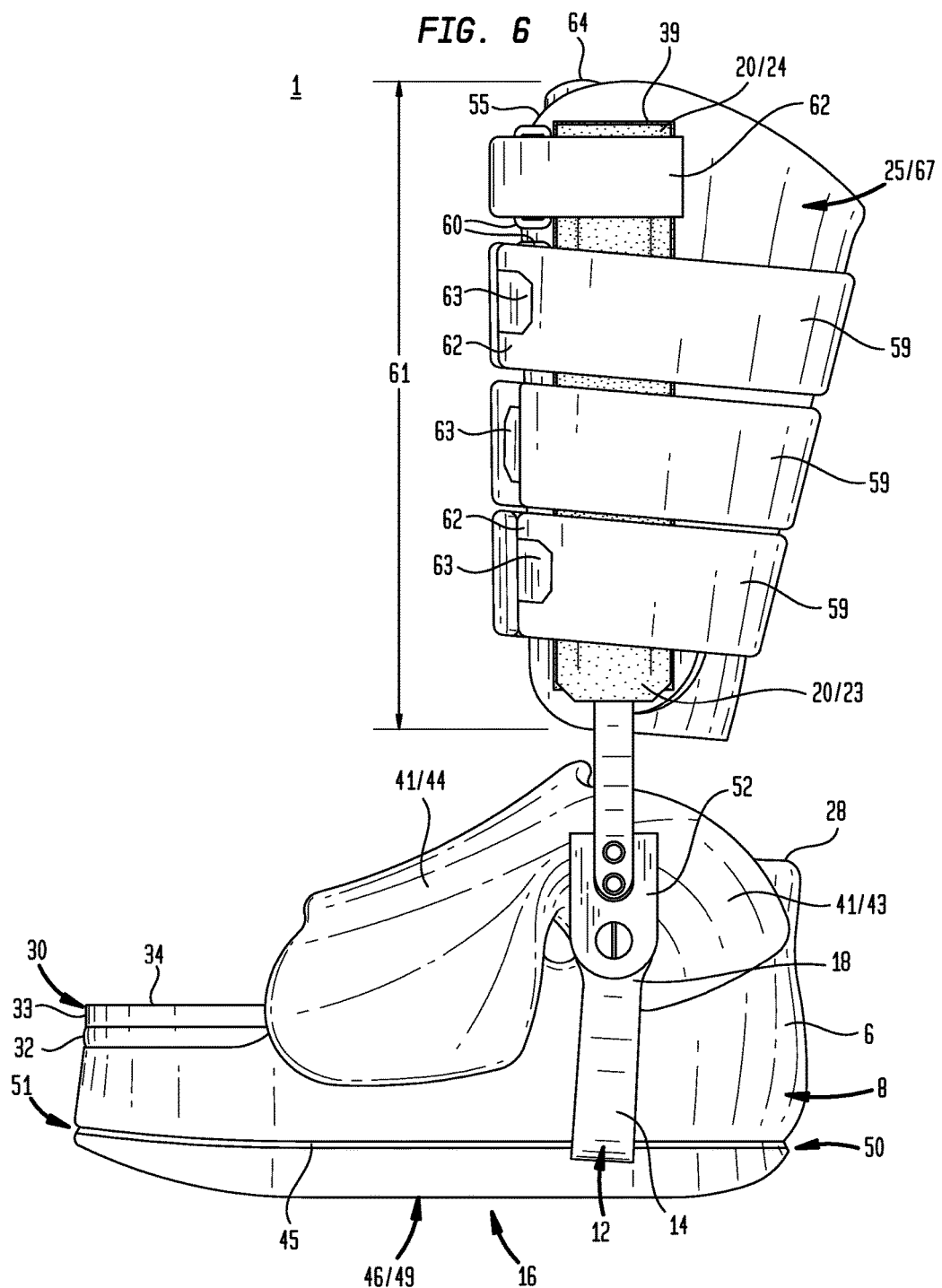
FIG. 6 is a medial side view of a particular embodiment of an inventive ankle-foot orthosis.
Figure 7:
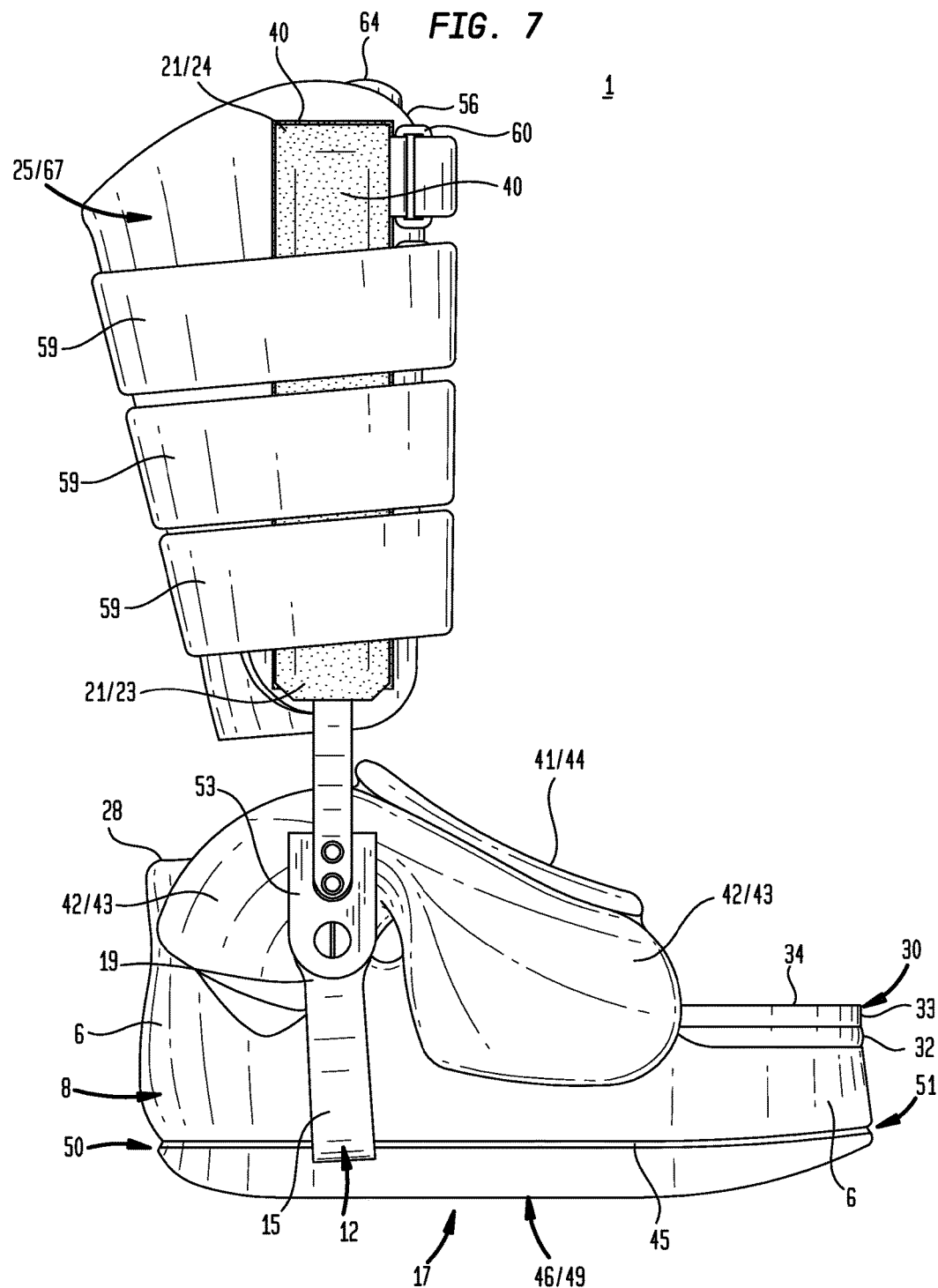
FIG. 7 is a lateral side view of a particular embodiment of an inventive ankle-foot orthosis.
Figure 8:
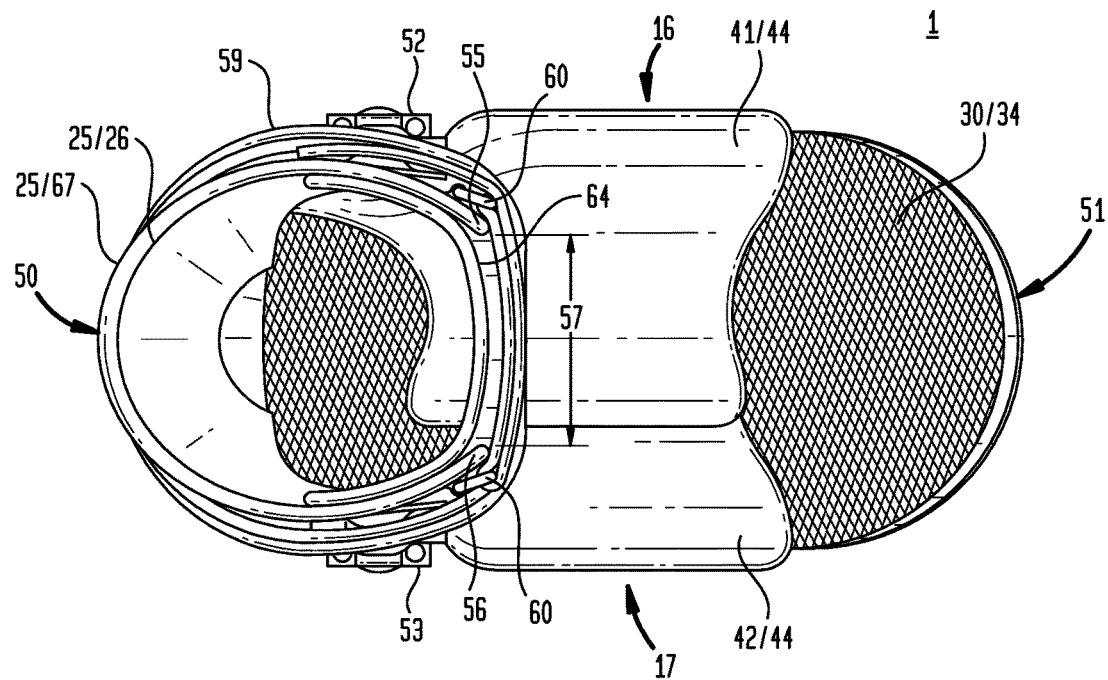
FIG. 8 is top view of a particular embodiment of an inventive ankle-foot orthosis.
Figure 9:
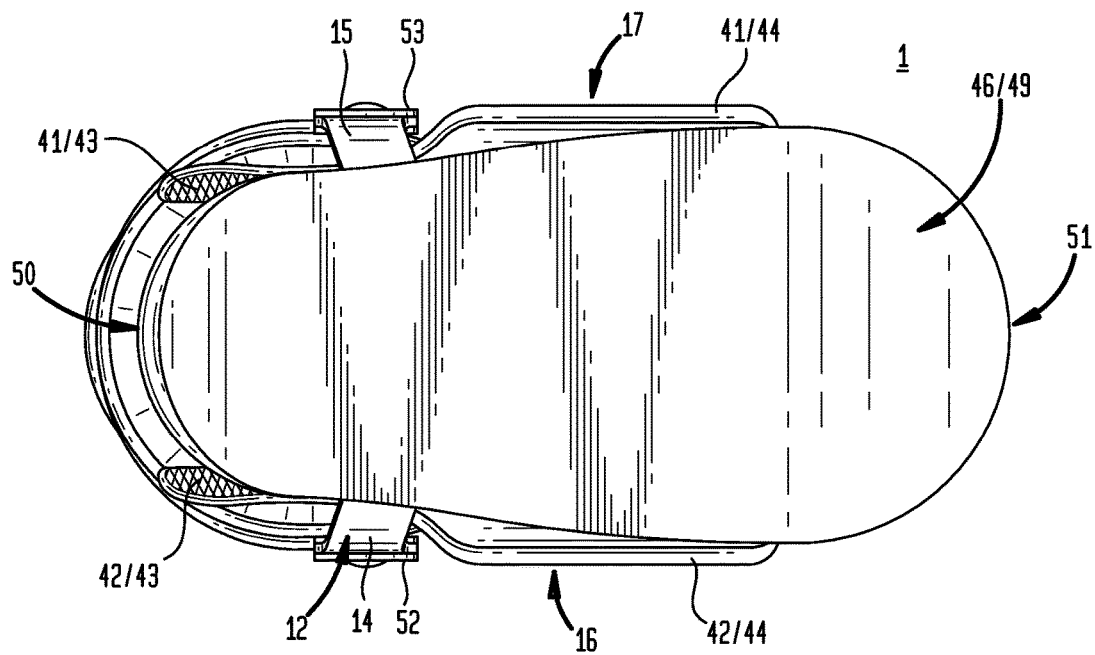
FIG. 9 is a bottom view of a particular embodiment of an inventive ankle-foot orthosis.

Again referring primarily to FIG. 2, embodiments of the invention can further include an outsole (46) secured to the insole (7) or the midsole (45), depending upon the embodiment, overlaying the stirrup base (13). A stirrup base recess (47) can be disposed in an outsole upper face (48) of the outsole (46). The stirrup base recess (47) can be configured to allow the stirrup base (13) to be disposed at a level flush or below the level of the outsole upper face (48) allowing the outsole upper face (48) to be secured to the insole (7) or the midsole (45) unobstructed by the thickness of the stirrup base (13). The outsole (46) can be made from one or more layers. The outsole (46) can be secured to the insole (7) or the midsole (45) by adhesive, stitching, mechanical fasteners, or other suitable securement means. The insole (7), midsole (45) and the outsole (46) can be made from natural materials such as leather or natural rubber, or from synthetic materials such as styrene butadiene rubber, nitrile-butdiene rubber, polyvinyl chloride, polyurethane, neoprene, polyether, polyester, or the like, or combinations thereof, whether as a solid material or as a foam, thermofoam, closed cell foam, or layers or combinations thereof. Portions of the outsole outer face (49) can be configured to curve toward the insole (7) approaching the outsole heel (50) or to the outsole toe (51) (as shown in the examples of FIGS. 6 and 7).

Again referring primarily to FIGS. 1 and 2, particular embodiments of the orthosis (1) can further include a pair of joint elements (52)(53) which correspondingly couple to the pair of stirrup ends (18)(19) and the brace first member ends (23). The pair of joint elements (52)(53) can rotationally couple the pair of stirrup ends (18)(19) to the corresponding brace first member ends (23) allowing movement of the pair of brace members (20)(21) about an axis (54) which extends through the pair of stirrup ends (18)(19) (as shown in the example of FIG. 2). As to particular embodiments, the pair of joint elements allow or can be adjusted to allow movement of the pair of braces (20)(21) from the substantially vertical position (as shown for example in FIG. 2) only toward the outsole toe (51), or only toward the outsole heel (50), or in both directions. As to particular embodiments, pair of joint elements (52)(53) can each be adjusted to limit the range of movement of over pre-determined angle of rotation bout the axis (54) to allow a corresponding predetermined amount of dorsiflexion or plantarflexion of the wearer's foot (3) within the combination (8).

Again referring primarily to FIGS. 1 through 9, as to particular embodiments, the cuff member (25) releasably secures to the pair of brace members (20)(21) which allows the cuff member (25) to be adjustably positioned along the brace length (22) of each of said pair of brace members (20)(21). As to the particular embodiments, the pair of brace members (20)(21) and said cuff member (25) further include mateable portions of hook and loop fasteners (39)(40) which releasably secure the cuff member (25) to the pair of brace members (20)(21). The cuff member (25) has an cuff internal surface (26) configured to releasably secure about the wearer's calf (5), as above described, to dispose a pair of cuff edges (55)(56) in opposed relation a distance (57) apart over the wearer's shin (58). A plurality of straps (59) operate to act on the cuff member (25) to reduce the distance (57) between the pair of cuff edges (55)(56) to secure the cuff member (25) about the wearer's calf (5). As to particular embodiments, a tongue (64) configured to engage the wearer's shin (58) can underlay the pair of cuff edges (55)(56) which can be drawn over the surface of the tongue (64). As to the embodiment shown in the Figures, a plurality of pairs of annular members (60) can be correspondingly secured to the pair of cuff edges (55)(56) along the height (61) of the cuff member (25). Each strap first end (62) can be secured to a first one of each of the pairs of annular members (60). Each strap second end (63) can pass through the second one of the pair of annular members (60) and each of the plurality of straps (59) drawn upon itself to reduce the distance (57) between the cuff edges (55)(56) and engage the cuff member (25) with the wearer's calf (5). Each of the plurality of straps (59) can be wrapped about the cuff member (25) with at least one overlaying the pair of braces (20)(21). Each strap second end (62) can releasably fasten to maintain the reduced distance (57) between opposed cuff edges (55)(56) and engagement of the cuff member (25) with the wearer's calf (5). As to the embodiment shown in the Figures, each of the plurality of straps (59) provides a loop material (39) and each second end (62) provides hook fasteners (40). Upon wrapping each of the plurality of straps (59) about the cuff member (25) the hook fasteners (40) can be releasably secured to the loop material (39) to secure the cuff member (25) to the wearer's calf (5).

Now referring primarily to FIGS. 10-13, which illustrate a particular method of fitting an orthosis (1) to transfer a portion of a wearer's weight (2) normally applied to a wearer's foot (3) to a wearer's calf (5). Transferring a portion a wearer's weight (2) normally applied to a wearer's foot (3) to a wearer's calf (5) removes weight bearing stress from the wearer's foot (3) and ankle (4). Embodiments of the method include providing an orthosis (1) in a form above described, securing the cuff member (25) about the wearer's calf (5), and placing the wearer's foot (3) in the combination (8), and securing the cuff member (25) to each of said pair of brace members (20)(21) at a position which transfers the portion of the wearer's weight (2) normally applied to the wearer's foot (3) to the wearer's calf (5), thereby removing weight bearing stress from the wearer's foot (3) and ankle (4).

Figure 10:
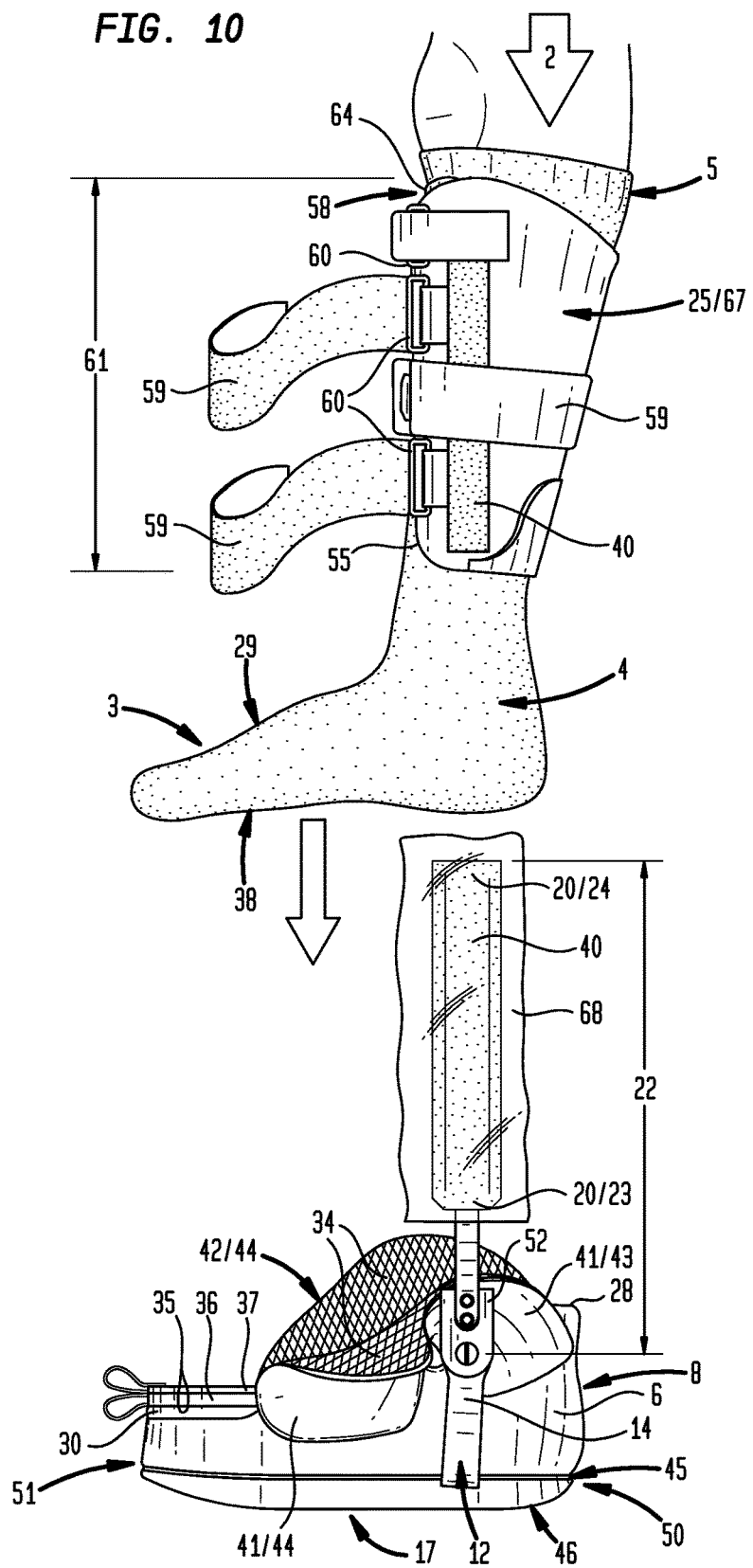
FIG. 10 is an illustration of a step in fitting a wearer to a particular embodiment of the inventive ankle-foot orthosis in which a cuff member secures to the wearer's calf and the wearer's foot is received within a combination of an upper secured to an insole to engage one or more fitting pads position within the combination.

The cuff member (25) can be secured about the wearer's calf (5) (or socked calf as shown in the example of FIG. 10) by wrapping at least one of said plurality of straps (59) about the cuff member (25). The tongue (64) can be disposed over the wearer's shin (58) underling the pair of cuff edges (55)(56) of the cuff member (25). One or more of the plurality of straps (59) can act on the cuff member (25) to sufficiently reduce the distance (57) between the pair of cuff edges (55)(56) to secure the cuff member (25) about the wearer's calf (5) (as shown in the example of FIG. 10). With flap second portions (44) opened the wearer's foot (3) can be received in the combination (8) atop the one or more fitting pads (35). As to particular embodiments, each of the pair of brace members (20)(21) can be inserted in a tubular cover

Figure 11:
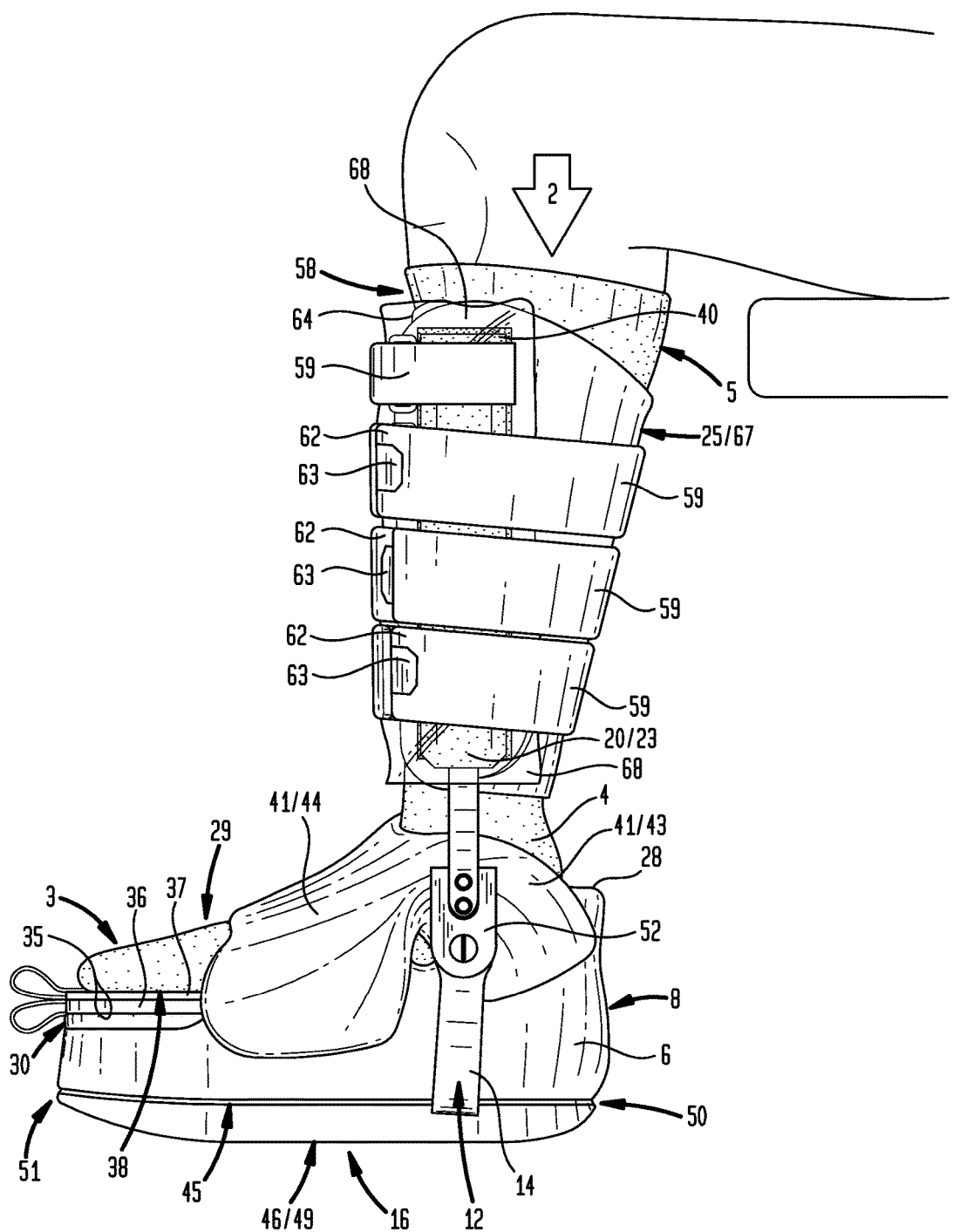
FIG. 11 is an illustration of a step in fitting a wearer to a particular embodiment of the inventive ankle-foot orthosis in which the cuff member is positioned in relation to a pair of brace members extending upwardly to positions adjacent each side of the wearer's calf.
Figure 12:
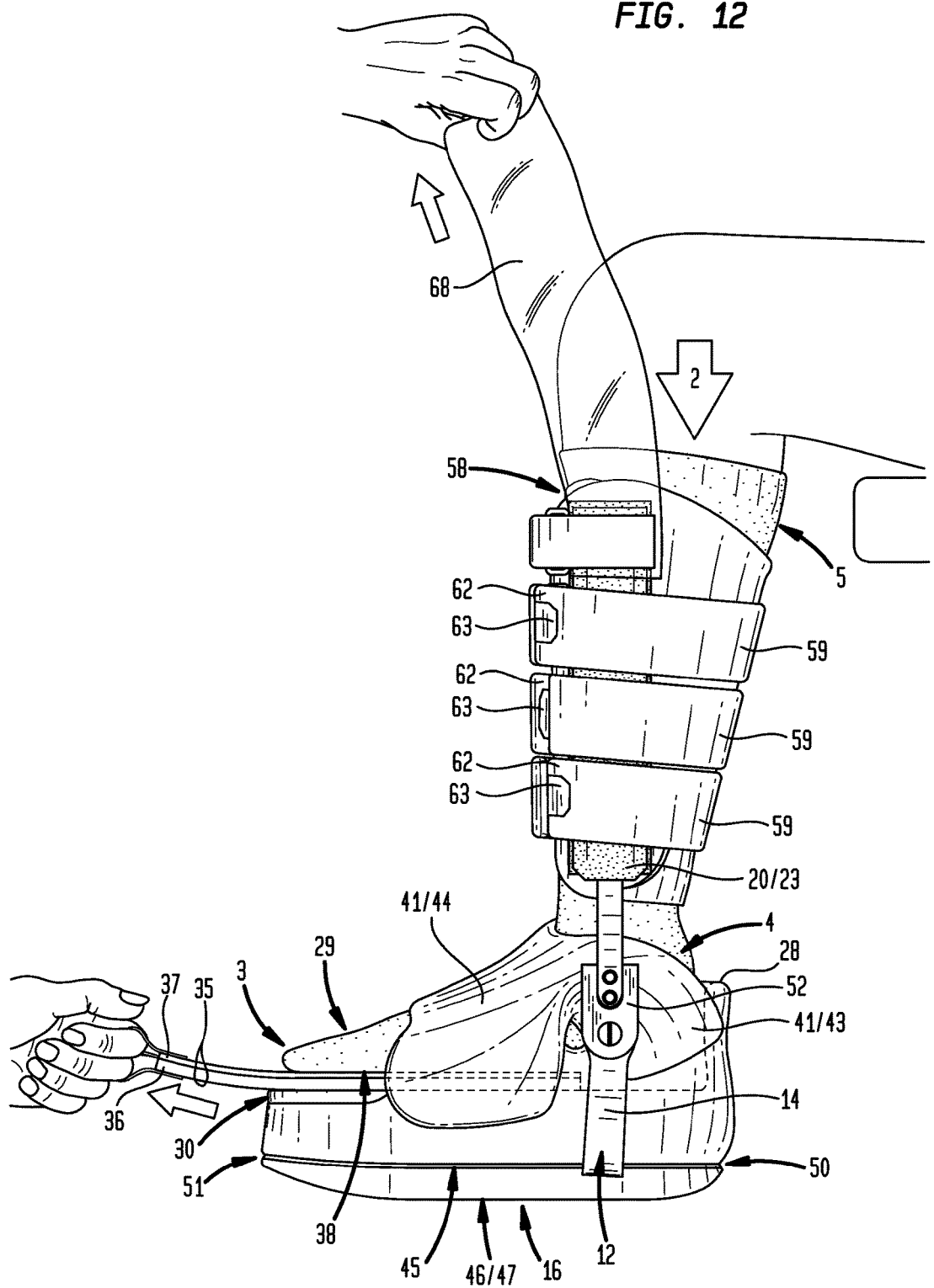
FIG. 12 is an illustration of a step in fitting a wearer to a particular embodiment of the inventive ankle-foot orthosis in which the cuff member is secured to the pair of brace members and the one or more fitting pads are removed from the combination.
Figure 13:
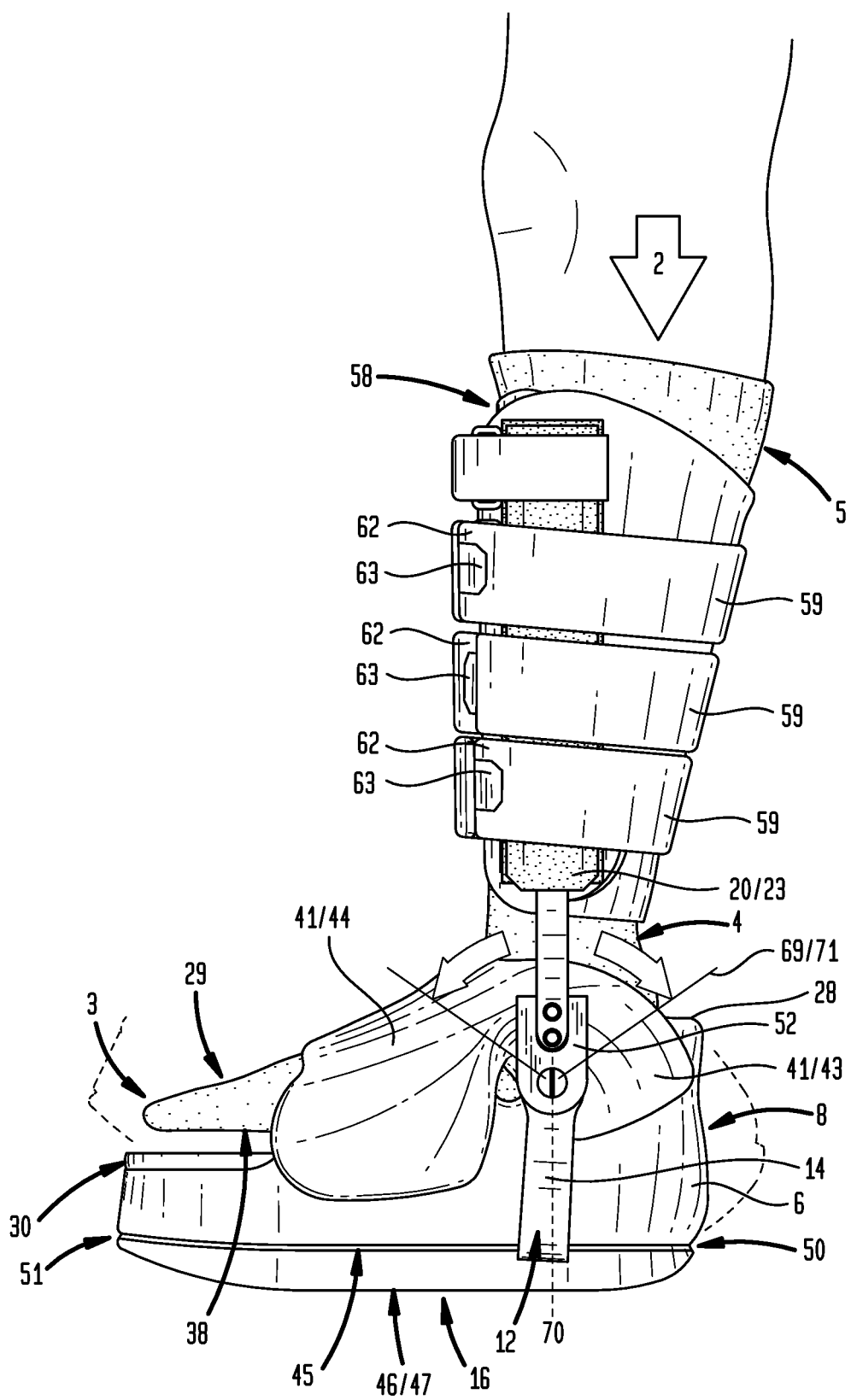
FIG. 13 is an illustration of a step in fitting a wearer to a particular embodiment of the inventive ankle-foot orthosis in which a portion of the wearer's weight normally applied to a wearer's foot and ankle is transferred to the wearer's calf to suspend the wearer's foot or in part remove weight bearing stress from the wearer's foot and ankle.

(68) (or other barrier element) to act as a barrier to the engagement of the pairs of hook and loop fasteners (39)(40) coupled respectively on the brace inside surfaces (65)(66) of the pair of brace members (20)(21) and the cuff member external surface (67) (as shown in the example of FIG. 10). Consequently, the cuff member (25) can be slidy engaged between the pair brace members (20)(21) to allow the wearer's foot (3) to be received within the combination (8) atop the one or more fitting pads (35)(as shown by the example of FIG. 11). With the cuff member (25) positioned in relation to the pair of brace members (20)(21), the a flap second portions (44) of the pair of dorsum flaps (41)(42) can be releasably secured in overlaid relation over the dorsum (29) of the wearer's foot (3) received in the combination (8). The plurality of straps (59) can be further drawn about the cuff member (25) to reduce the distance (57) between the pair of cuff edges (55)(56) to secure the cuff member (25) about the wearer's calf (5) and by wrapping at least one of the plurality of strap members (59) about the pair of brace members (20)(21) the cuff member (25) can be secured in fixed relation to the pair of brace members (20)(21) (as shown by the example of FIG. 11). With the cuff member (25) adjacent to the vertically extending, upright pair of brace members (20)(21), the tubular cover (68) (or other barrier element) acting as a barrier to the securement of the pairs of hook and loop fasteners (39)(40) can be removed (as shown in the example of FIG. 12) to secure the hook and loop fasteners (39)(40) securing the cuff member (25) to the pair of brace members (20)(21). Subsequently, the one or more fitting pads (35) can be removed (as shown in the example of FIG. 12). The wearer's foot (3) can now be suspended in relation to the insole (7) or the main pad (30) or at least a portion of the wearer's weight (2) normally applied to the wearer's foot (3) is transferred to and borne by the wearer's calf (5) by engagement with the cuff member (25) secured to the pair of brace members (20)(21). As to particular embodiments, the pair of joint elements (52)(53) correspondingly coupled between said pair of stirrup ends (18)(19) and the pair of brace members (20)(21) can be adjusted to provide a range of movement (69) of the pair of brace members (20) (21) in relation to the combination (8), whether movement from a generally vertical position (70) only toward the outsole toe (51) (or toward the toe of the combination (8)), or from a generally vertical position (70) only toward the outsole heel (50) (or toward the heel of the combination (8)), or throughout a pre-adjusted fixed angle of movement (71). The range of movement (69) can be selected by adjustment of the pair of joint elements (52)(53) to allow a pre-determined amount of dorsiflexion and plantarflexion of the wearer's foot (3) (as shown in the example of FIG. 13).

Consequently, the wearer's foot (3) does not bear the normal wearer's weight (2) and the dorsiflexion and plantarflexion of the wearer's foot (3) can be restricted to a pre-adjusted fixed angle of movement (71) useful in treatment of the wearer's foot (3) and ankle (4). The portion of the wearer's weight (2) transferred to the wearer's calf (5) during a normal stride with the other foot off the ground could be virtually any percentage, but preferably is in the range of about 10% to about 75% and more preferably in the range of about 40% to about 60%. In most cases, the higher the percentage of weight transferred the better including up to 100%. As to particular applications, the wear's foot (3) or heel (as shown in the example of FIG. 13) can be spaced or suspended above the main pad (30), for example about one-quarter inch to about one-half inch.

As can be easily understood from the foregoing, the basic concepts of the present invention may be embodied in a variety of ways. The invention involves numerous and varied embodiments of a reciprocally telescoping door stop and methods for making and using such door stops including the best mode.

As such, the particular embodiments or elements of the invention disclosed by the description or shown in the figures or tables accompanying this application are not intended to be limiting, but rather exemplary of the numerous and varied embodiments generically encompassed by the invention or equivalents encompassed with respect to any particular element thereof. In addition, the specific description of a single embodiment or element of the invention may not explicitly describe all embodiments or elements possible; many alternatives are implicitly disclosed by the description and figures.

It should be understood that each element of an apparatus or each step of a method may be described by an apparatus term or method term. Such terms can be substituted where desired to make explicit the implicitly broad coverage to which this invention is entitled. As but one example, it should be understood that all steps of a method may be disclosed as an action, a means for taking that action, or as an element which causes that action. Similarly, each element of an apparatus may be disclosed as the physical element or the action which that physical element facilitates. As but one example, the disclosure of a "brace" should be understood to encompass disclosure of the act of "bracing"—whether explicitly discussed or not—and, conversely, were there effectively disclosure of the act of "bracing", such a disclosure should be understood to encompass disclosure of a "brace" and even a "means for bracing." Such alternative terms for each element or step are to be understood to be explicitly included in the description.

In addition, as to each term used it should be understood that unless its utilization in this application is inconsistent with such interpretation, common dictionary definitions should be understood to included in the description for each term as contained in the Random House Webster's Unabridged Dictionary, second edition, each definition hereby incorporated by reference.

All numeric values herein are assumed to be modified by the term "about", whether or not explicitly indicated. For the purposes of the present invention, ranges may be expressed as from "about" one particular value to "about" another particular value. When such a range is expressed, another embodiment includes from the one particular value to the other particular value. The recitation of numerical ranges by endpoints includes all the numeric values subsumed within that range. A numerical range of one to five includes for example the numeric values 1, 1.5, 2, 2.75, 3, 3.80, 4, 5, and so forth. It will be further understood that the endpoints of each of the ranges are significant both in relation to the other endpoint, and independently of the other endpoint. When a value is expressed as an approximation by use of the antecedent "about," it will be understood that the particular value forms another embodiment. The term "about" generally refers to a range of numeric values that one of skill in the art would consider equivalent to the recited numeric value or having the same function or result. Similarly, the antecedent "substantially" means largely, but not wholly, the same form, manner or degree and the particular element will have a range of configurations as a wearer of ordinary skill in the art would consider as having the same function or result. When a particular element is expressed as an approximation by use of the antecedent "substantially," it will be understood that the particular element forms another embodiment.

Moreover, for the purposes of the present invention, the term "a" or "an" entity refers to one or more of that entity unless otherwise limited. As such, the terms "a" or "an", "one or more" and "at least one" can be used interchangeably herein.

Thus, the applicant(s) should be understood to claim at least: i) each of the ortosis herein disclosed and described, ii) the related methods disclosed and described, iii) similar, equivalent, and even implicit variations of each of these devices and methods, iv) those alternative embodiments which accomplish each of the functions shown, disclosed, or described, v) those alternative designs and methods which accomplish each of the functions shown as are implicit to accomplish that which is disclosed and described, vi) each feature, component, and step shown as separate and independent inventions, vii) the applications enhanced by the various systems or components disclosed, viii) the resulting products produced by such systems or components, ix) methods and apparatuses substantially as described hereinbefore and with reference to any of the accompanying examples, x) the various combinations and permutations of each of the previous elements disclosed.

The background section of this patent application provides a statement of the field of endeavor to which the invention pertains. This section may also incorporate or contain paraphrasing of certain United States patents, patent applications, publications, or subject matter of the claimed invention useful in relating information, problems, or concerns about the state of technology to which the invention is drawn toward. It is not intended that any United States patent, patent application, publication, statement or other information cited or incorporated herein be interpreted, construed or deemed to be admitted as prior art with respect to the invention.

The claims set forth in this specification, if any, are hereby incorporated by reference as part of this description of the invention, and the applicant expressly reserves the right to use all of or a portion of such incorporated content of such claims as additional description to support any of or all of the claims or any element or component thereof, and the applicant further expressly reserves the right to move any portion of or all of the incorporated content of such claims or any element or component thereof from the description into the claims or vice-versa as necessary to define the matter for which protection is sought by this application or by any subsequent application or continuation, division, or continuation-in-part application thereof, or to obtain any benefit of, reduction in fees pursuant to, or to comply with the patent laws, rules, or regulations of any country or treaty, and such content incorporated by reference shall survive during the entire pendency of this application including any subsequent continuation, division, or continuation-in-part application thereof or any reissue or extension thereon.

Additionally, the claims set forth in this specification, if any, are further intended to describe the metes and bounds of a limited number of the preferred embodiments of the invention and are not to be construed as the broadest embodiment of the invention or a complete listing of embodiments of the invention that may be claimed. The applicant does not waive any right to develop further claims based upon the description set forth above as a part of any continuation, division, or continuation-in-part, or similar application.

I claim:

1. An orthosis comprising:
   an upper secured to an insole in a combination having a configuration adapted to receive a wearer's foot;
   an outsole secured to said insole;
   a stirrup base recess disposed in an outsole upper face of said outsole; and
   a stirrup including a stirrup base connected between a pair of stirrup side pieces,
   said stirrup base disposed in said stirrup base recess between said insole and said outsole, said pair of stirrup side pieces each upwardly extending to positions adjacent each side of said combination.

2. The orthosis of claim 1, further comprising a midsole disposed between said insole and said outsole.

3. The orthosis of claim 1, further comprising a forefoot portion of said outsole, said forefoot portion curved toward said insole approaching a toe of said combination.

4. The orthosis of claim 1, further comprising a pair of dorsum flaps each having a flap first portion releasably securable at a position adjacent corresponding sides of said upper, said pair of dorsum flaps each having a flap second portion configured to releasably secure in overlaid relation over a dorsum of said wearer's foot received within said combination.

5. The orthosis of claim 4, wherein each of said first portions of said pair of dorsum flaps adjustably position adjacent corresponding said sides of said upper.

6. The orthosis of claim 5, wherein said upper releasably secures hook fasteners mounted on said flap first portion.

7. The orthosis of claim 6, wherein said flap second portions further include mateable portions of hook and loop fasteners which releasably secure said second portions in overlaid relation over said dorsum of said wearer's foot received within said combination.

8. The orthosis of claim 1, further comprising a pair of brace members each having a length disposed between a brace member first end and a brace member second end, said brace member first ends correspondingly coupled to a pair of stirrup ends of said pair of stirrup side pieces, said pair of brace members configured to extend upwardly to positions adjacent each side of said wearer's calf.

9. The orthosis of claim 8, further comprising a cuff member having a cuff member external surface securable to said pair of brace members, said cuff member having a cuff member internal surface configured to secure to said wearer's calf to allow transfer of a portion of said wearer's weight normally applied to the foot to said wearer's calf.

10. The orthosis of claim 9, wherein said pair of brace members and said cuff member further include mateable portions of hook and loop fasteners which releasably secure said cuff member to said pair of brace members.

11. The orthosis of claim 9, wherein said cuff member has a configuration which releasably secures about said wearer's calf to dispose a pair of cuff edges in opposed relation a distance apart and further comprising a plurality of straps which act on said cuff member to reduce said distance between said pair of cuff edges to secure said cuff member about said wearer's calf.

12. The orthosis of claim 11, wherein one or more of said plurality of straps releasably secures about said pair of braces.

13. The orthosis of 12, further comprising a tongue underlying said pair of cuff edges, said tongue configured to overlay said wearer's shin.

14. The orthosis of claim 13, further comprising an antimicrobial lining coupled to said tongue which is adapted to engage said wearer's tibia received within said cuff.

15. The orthosis of claim 8, further comprising a pair of joint elements which correspondingly couple said pair of stirrup ends of said pair of stirrup side pieces and said brace member first ends.

16. The orthosis of claim 15, wherein said pair of joint elements pivotally couple said pair of stirrup ends to said brace member first ends allowing rotation of said pair of brace members about a pivot axis extending through said pair of stirrup ends to allow corresponding dorsiflexion and plantarflexion of said wearer's foot within said combination.

17. The orthosis of claim 1, further comprising a main pad engaging said insole within said combination.

18. The orthosis of claim 17, further comprising one or more fitting pads which removably overlay said main pad.

19. The orthosis of claim 18, further comprising an antimicrobial lining coupled to said main pad which is adapted to engage said wearer's foot received within said combination.

20. The orthosis of claim 1, further comprising an antimicrobial lining coupled to an upper inner surface of said upper which is adapted to engage said wearer's foot received within said combination.

21. The orthosis of claim 1, wherein said stirrup base recess disposed in said outsole upper face allows disposition of said stirrup base at a level flush with or below said outsole upper face.

22. An orthosis comprising:
- an upper secured to an insole in a combination having a configuration adapted to receive a wearer's foot;
- an outsole secured to said insole;
- a midsole disposed between said insole and said outsole;
- a stirrup including a stirrup base connected between a pair of stirrup side pieces;
- said stirrup base disposed between said midsole and said outsole;
- said pair of stirrup side pieces each upwardly extending to positions adjacent each side of said combination; and
- a stirrup base recess disposed in a midsole first face of said midsole;
- said stirrup base recess configured to receive said stirrup base.

23. The orthosis of claim 22, wherein said stirrup base recess disposed in said midsole first face allows disposition of said stirrup base at a level flush with or above said midsole first face.

\* \* \* \* \*